United States Patent [19]

Markert et al.

[11] Patent Number: 4,904,640
[45] Date of Patent: Feb. 27, 1990

[54] 2-ALKYLIDENE-3,3,5(3,5,5)-TRIMETHYL CYCLOPENTANONES

[75] Inventors: Thomas Markert, Duesseldorf; Klaus Bruns, Krefeld-Traar; Horst-Juergen Krause, Duesseldorf; Josef Penninger, Hilden, all of Fed. Rep. of Germany; Michael Virnig, Santa Rosa, Calif.; Volker Falk, Velbert, Fed. Rep. of Germany

[73] Assignee: Henkel Kommanditgesellschaft auf Aktien, Duesseldorf, Fed. Rep. of Germany

[21] Appl. No.: 164,159

[22] Filed: Mar. 4, 1988

[30] Foreign Application Priority Data

Mar. 6, 1987 [DE] Fed. Rep. of Germany ....... 3707209

[51] Int. Cl.$^4$ ................................................ A61K 7/46
[52] U.S. Cl. ........................................ 512/8; 568/379
[58] Field of Search ............................ 568/374; 512/8

[56] References Cited

U.S. PATENT DOCUMENTS

| | | | |
|---|---|---|---|
| 2,069,861 | 2/1937 | St. Pfau | 260/131 |
| 3,639,428 | 2/1972 | Fried | 240/345.9 |
| 3,652,596 | 3/1972 | Fried | 260/340 |
| 3,773,789 | 11/1973 | Fried | 260/340.9 |
| 3,855,247 | 12/1974 | Fried | 260/340.9 |
| 3,880,884 | 4/1975 | Fried | 260/343.2 |
| 3,888,952 | 6/1975 | Fried | 260/951 |
| 3,979,458 | 9/1976 | Fried | 260/585 |
| 4,217,251 | 8/1980 | Dastur | 568/379 |
| 4,260,830 | 4/1981 | Wilson et al. | 568/485 |
| 4,310,701 | 1/1982 | Wilson et al. | 568/347 |
| 4,477,683 | 10/1984 | Virgilio et al. | 568/379 |
| 4,668,827 | 5/1987 | Tamura et al. | 568/345 |

FOREIGN PATENT DOCUMENTS

| | | | |
|---|---|---|---|
| 150051 | 8/1981 | Fed. Rep. of Germany | 568/379 |
| 3508420 | 9/1986 | Fed. Rep. of Germany | 568/345 |
| 2498592 | 7/1982 | France | 512/8 |
| 56-46833 | 4/1981 | Japan | 512/8 |

OTHER PUBLICATIONS

Helvetia Chimica Acta 16, 1208 (1933).

*Primary Examiner*—James H. Reamer
*Attorney, Agent, or Firm*—Ernest G. Szoke; Wayne C. Jaeschke; Henry E. Millson, Jr.

[57] ABSTRACT

2-Alkylidene-3,3,5(3,5,5)-trimethylcyclopentanones corresponding to the following general formula

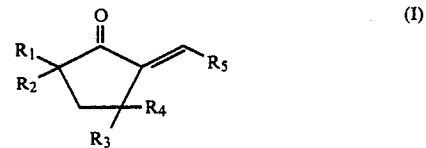

in which three of the substituents $R_1$ to $R_4$ are $CH_3$, one of the substituents $R_1$ to $R_4$ is H, and $R_5$ is a saturated or unsaturated, linear branched $C_1$-$C_7$ alkyl radical, and the double bond is in the endo position to the cyclopentanone structure. The compounds of formula (I) are useful as perfumes.

12 Claims, No Drawings

2-ALKYLIDENE-3,3,5(3,5,5)-TRIMETHYL CYCLOPENTANONES

BACKGROUND OF THE INVENTION

1. Field of the Invention

This invention releates to 2-alkylidene-3,3,5(3,5,5)-trimethyl cyclopentanones, to processes for their preparation, and to their use as perfumes.

2. Statement of Related Art

Jasmone, a major carrier of the jasmine odor, is present in the ethereal oils of Jasminum grandiflorum in quantities of about 3% and is said also to occur in very small quantities in orange blossom and jonquil extract oils (L. Ruzicka, M. Pfieffer in "Helvetica Chimica Acta" 16 108 (1933)). However, the preparation of relatively large quantities of this interesting perfume on the one hand requires very large quantities of jasmine blossoms while, on the other hand, the isolation of jasmone involves laborious and expensive process steps.

DESCRIPTION OF INVENTION

Other than in the operating examples, or where otherwise indicated, all numbers expressing quantities of ingredients or reaction conditions used herein are to be understood as modified in all instances by the term "about".

An object of the present invention is to provide synthetic substitute perfumes for jasmone which may readily be produced in large quantities on a commercial scale.

2-Benzyl-3,5,5-trimethylcyclopent-2-ene-1-one is known from Bulletin de la Société Chimique de France 1959, 493 to 496, being formed in the reaction of 3,5,5-trimethylcyclopent-2-ene-1-one with benzyl bromide in the presence of sodium tert.-amylate. None of the odor properties of this compound are mentioned.

The present invention is based on the surprising discovery that 2-alkylidene-3,3,5(3,5,5)-trimethyl cyclopentanones containing a saturated or unsaturated, linear or branched $C_1$–$C_7$ alkyl radical in the 2-position are suitable substitute perfumes for jasmone. They can readily be produced in large quantities on a commerical scale.

In the context of the invention, "2-alkylidene-3,3,5(3,5,5)-trimethyl cyclopentanones" are understood to be isomer mixtures consisting of 2-alkylidene-3-3,5-trimethyl cyclopentanones, or 2-alkylidene-3,5,5-trimethyl cyclopentanones and 2-alkyl-3,5,5-trimethyl-cyclopent-2-ene-1-ones, or 2-alkylidene-3,3,5-trimethyl cyclopentanones, 2-alkylidene-3,5,5-trimethyl cyclopentanones and 2-alkyl-3,5,5-trimethylcyclopent-2-ene-1-ones.

The present invention relates to 2-alkylidene-3,3,5(3,5,5)-trimethyl cyclopentanones corresponding to the following general formula

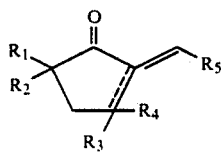

(I)

in which three of the substituents $R_1$ to $R_4$ are $CH_3$, one of the substituents $R_1$ to $R_4$ is H and $R_4$ is a saturated or unsaturated, linear or branched $C_1$–$C_7$ alkyl radical and the double bond is in the endo or exo position to the cyclopentanone structure.

The present invention also relates to a process for the preparation of 2-alkylidene-3,3,5(3,5,5)-trimethyl cyclopentanones corresponding to general formula (I) wherein, in an aldol condensation, 2,2,4-trimethyl cyLopentanone, 2,4,4-trimethyl cyclopentanone, or mixtures thereof, are reacted with an aldehyde $R_5$—CHO, preferably in excess, in the presence of a base, the reaction product is subsequently neutralized and, if desired, isomerized in the presence of hydrogen halide, preferably hydrogen bromide.

The present invention relates to another process for the preparation of 2-alkylidene-3,3,5(3,5,5)-trimethyl cyclopentanones of formula (I) in which, in an aldol condensation, 2,2,4-trimethyl cyclopentanone, 2,4,4-trimethyl cyclopentanone, or mixtures thereof are reacted with an aldehyde $R_5$—CHO, preferably present in excess, in the presence of a base and a phase transfer catalyst, the reaction mixture is extracted with an organic solvent, subsequently neutralized and dried, the residue is treated with a solvent which forms an azeotrope with water and also treated with an acidic catalyst, preferably p-toluenensulfonic acid and/or amidosulfonic acid, and, if desired, the reaction product obtained is isomerized in the presence of hydrogen halide, preferably hydrogen bromide.

More specifically, the cyclopentanones of formula (I) are prepared by aldol condensation by reaction of 2,2,4-trimethyl cyclopentanone, 2,4,4-trimethyl cyclopentanone, or mixtures thereof with an aldehyde $R_5$—CHO (preferably in excess), where $R_5$ is a saturated or unsaturated, linear or branched $C_1$–$C_7$ alkyl radical, in the presence of a base, preferably followed by stirring for 10 to 20 hours, more especially for 14 to 17 hours, at 20° to 25° C. Preferred bases are alkali metal hydroxides, methylates, ethylates, propylates and/or butylates. Sodium methylate is particularly preferred. The aldol condensation by which the cyclopentanones of the invention are prepared can also be carred out as follows: 2,2,4-trimethyl cyclopentanone, 2,4,4-trimethylcyclopentanone, or mixtures thereof are reacted with an aldehyde $R_5$—CHO (preferably in excess) in the presence of a base and a phase transfer catalyst, the reaction mixture is then left standing for 10 to 20 hours and more especially for 14 to 17 hours at 20° to 25° C., followed by extraction with organic solvents, for example diethyl ether, neutralization, for example by washing until neutral with an aqueous solution of sodium chloride, and drying, for example with anhydrous sodium, calcium and/or magnesium sulfate. The organic solvent is then removed, after which the residue is treated with a solvent which forms an azeotrope with water, for example toluene, and an acidic catalyst is added, preferably p-toluenesulfonic acid and/or amidosulfonic acid, at the boiling temperature of the solvent. Alkali metal hydroxides are preferably used as the bases, potassium hydroxide being particularly preferred. Crown ethers and/or polyalkyleneglycols are preferred phase transfer catalysts. Polyethyleneglycols having average molecular weights of 400 to 1,000 are particularly preferred. The aldol condensations are preferably carried out at 20° to 30° C. The neutralized reaction products freed from solvents contain, inter alia, 2-alkylidene-3,5,5-trimethyl cyclopentanone, i.e. a trimethyl cyclopentanone derivative with an exocyclic double bond. To obtain reaction products having a relatively high content of trimethyl cyclopentanone derivatives with an endocyclic double bond, i.e. with a relatively high content of 2-alkyl-3,5,5-trimethylcyclopent-2-ene-1-one, an isomerization may be carried out in the presence of hydrogen halides, for example hydrogen bromide, at 80° to 85° C. (L. -F. Tietze, Th. Eicher in "Reaktionen und Synthesen", page 162, Thieme-Verlag Stuttgart 1981).

The present invention also relates to the use of the 2-alkylidene-3,3,5(3,5,5)-trimethyl cyclopentanones of formula (I) as perfumes.

2-Alkylidene-3,3,5(3,5,5)-trimethyl cyclopentanones of formula (I) containing 2 to 5 C atoms in the saturated or unsaturated, linear or branched $R_5$ radical are preferred. 2-Alkylidene-3,3,5(3,5,5)-trimethyl cyclopentanones containing 3 C atoms in the saturated or unsaturated, linear or branched $R_5$ radical, for example 2-n-butylidene-3,3,5(3,5,5)-trimethyl cyclopentanone, are particularly preferred.

The 2-alkylidene-3,3,5(3,5,5)-trimethyl cyclopentanones of formula (I) are excellent jasmone perfumes with a very harmonious odor profile. They can be used either on their own or in combination with other perfumes for perfuming, for example, cosmetics, such as scents, creams, lotions, aerosols and toilet soaps, in extract perfumery, for the odor enhancement of commercial products, such as cleaning preparations and disinfectants, and in fabric treatment preparations.

The perfumes of formula (I) ar present in perfume compositions in quantities of from 1 to 50% by weight and preferably in quantities of from 2 to 25% by weight.

The invention will be illustrated but not limited by the following examples.

EXAMPLES

Example 1

2-n-butylidene-3,5,5(3,3,5)-trimethyl cyclopentanone

| Constituents | | |
| --- | --- | --- |
| I | 170.37 g (1.35 mol) | 2,2,4(2,4,4)-trimethylcyclopentanone (isomer ration 57.5:42.5) |
| II | 72 g (0.4 mol) | sodium methylate, 30% |
| III | 71 g (0.5 mol) | sodium sulfate, anhydrous |
| IV | 194.7 g (2.7 mol) | n-butanal |

Procedure:

IV was continuously added dropwise under nitrogen and with stirring to a mixture of I, II and III over a period of 6 hours. After stirring overnight, the reaction mixture was neutralized with dilute $H_2SO_4$. The reaction mixture, which contained precipitated salts, was diluted with water, the aqueous phase was separated off and the organic phase concentrated. The residue was distilled. Yield: 124.3 g, corresponding to 51.1% of the theoretical. Bp.: 55°-80° C./0.9 mbar. Odor: jasmone, celery, lovage.

EXAMPLE 2

2-n-butylidene-3,3,5(3,5,5)-trimethyl cyclopentanone

| Constituents | | |
| --- | --- | --- |
| I | 126.6 g (1 mol) | 2,2,4(2,4,4)-trimethylcyclopentanone (isomer ratio 57.5:42.5) |
| II | 26.4 g (0.4 mol) | potassium hydroxide, 85% |
| III | 5.2 g | polyethyleneglycol, average molecular weight 600 |
| IV | 44.17 g (0.35 mol) | 2,2,4(2,4,4)-trimethylcyclopentanone (isomer ratio 57.5:42.5) |
| V | 97.3 g (1.35 mol) | n-butanal |
| VI | 0.2 g | p-toluenesulfonic acid monohydrate |

Procedure:

A mixture of IV and V was continuously added under nitrogen and with stirring to I, II and III over a period of 6 hours. After standing overnight, the reaction mixture was not neutralized, but instead was extracted with ether, washed with saturated sodium chloride solution until neutral, and concentrated after drying over $Na_2SO_4$. The residue was taken up in toluene and heated to the reflux temperature on a water separator with 0.2 g VI.

7.8 ml water were distilled off azeotropically. After VI had been washed out, the toluene was distilled off and the residue fractionated. Yield: 71.9 g, corresponding to 29.5% of the theoretical.

Example 3

2-n-butyl-3,5,5-trimethylcyclopent-2-ene-1-one from 2-n-butylidene-3,3,5(3,5,5)-trimethyl cyclopentanone by isomerization

| Constituents | | |
| --- | --- | --- |
| I | 50 g | 2-n-butylidene-3,3,5(3,5,5)-trimethylcyclopentanone prepared in accordance with Example 1 |
| II | 300 ml | n-butanol |
| III | 50 ml | hydrobromic acid, 48% |

Procedure:

I and II were mixed and heated with stirring under nitrogen to 80° C. III was then slowly added dropwise, followed by heating under reflux for 14 hours. After cooling, the reaction mixture was extracted with ether, washed until neutral, dried, concentrated, and distilled. An isomer mixture in which the ratio of endocyclic to exocyclic compound is 28.4:51.6% was obtained in a yield of 48 g. Bp.: 52°-53° C./1 mbar. Odor: jasome, cord note.

Example 4

2-n-pentylidene-3,5,5(3,3,5)-trimethyl cyclopentanone

| Constituents | | |
| --- | --- | --- |
| I | 94.7 g (0.75 mol) | 2,2,4(2,4,4)-trimethylcyclopentanone (isomer ratio 57.5:42.5) |
| II | 54 g (0.3 mol) | sodium methylate, 30% |
| III | 53.3 g (0.375 mol) | sodium sulfate, anhydrous |
| IV | 31.6 g (0.25 mol) | 2,2,4(2,4,4)-trimethylcyclopentanone (isomer ratio 57.5:42.5) |
| V | 172.2 g (2 mol) | n-pentanal |

Procedure:

I, II and III were stirred under nitrogen at 22° C. and a mixture of IV and V was added dropwise over a period of 6 hours. After stirring overnight, the reaction mixture was neutralized with dilute sulfuric acid. Precipitated salts were dissolved by addition of water, the aqueous phase was separated off and the organicphase concentrated, followed by distillation and fractionation. Yield: 95 g, corresponding to 48.9% of the theoretical. Boiling point of the pentylidene compound: 60°-70° C./1 mbar. Odor: jasmone note, fruity.

Example 5

2-n-butylidene-3,5,5-trimethyl cyclopentanone

| Constituents | | |
|---|---|---|
| I | 40 g (0.318 mol) | 2,2,4-trimethylcyclopentanone, 100% |
| II | 17.1 g (0.095 mol) | sodium methylate, 30% |
| III | 17 g (0.12 mol) | sodium sulfate, anhydrous |
| IV | 46.2 g (0.64 mol) | n-butanal |

Procedure as in Example 1. Yield: 42.3 g, corresp5 to 73.3% of the theoretical. Bp.: 60°–63° C./1 mbar. Odor: fine jasmine, cord note.

Example 6

2-n-butylidene-3,3,5-trimethyl cyclopentanone

| Constituents | | |
|---|---|---|
| I | 40.0 g (0.318 mol) | 2,4,4-trimethylcyclopentanone, 99.9% |
| II | 18.1 g (0.095 mol) | sodium methylate, 30% |
| III | 17 g (0.12 mol) | sodium sulfate, anhydrous |
| IV | 46.2 g (0.64 mol) | n-butanal |

Procedure as in Example 1. Yield: 27.2 g, corresponding to 47% of the theoretical. Bp.: 63°–65° C./1 mbar. Odor: emanative celery, lovage note, spicy, green.

COMPOSITION EXAMPLES

| Jasmine harmony | Part by weight |
|---|---|
| Methyl cyclooctyl carbonate (Jasmacyclat $^{(R)}$, Henkel KGaA) | 330 |
| α-hexyl cinnamaldehyde | 200 |
| Linalool | 60 |
| Linalyl acetate | 60 |
| Hydroxy citronellal | 60 |
| Benzyl acetate | 50 |
| 2-n-butylidene-3,5,5(3,5,5)-trimethylcyclopentanone, prepared in accordance with Ex. 1 | 50 |
| Benzyl salicylate | 50 |
| Ylang oil | 40 |
| Geranyl acetate | 25 |
| α-Methyl-β(p-tert.-butylphenyl-propionaldehyde | 20 |
| Phenyl ethyl acetate | 20 |
| Methyl ionone mixture (Isoraldein TM 70) | 15 |
| p-Cresyl phenyl acetate, 10% in diethyl phthalate | 15 |
| 6-(Spiroendomethylene-1,4-cyclohexyl-2)-tetrahydropyran (Mugoflor TM, H & R) | 5 |

| Rose-jasmine harmony | Part by weight |
|---|---|
| Citronellol | 230 |
| Hexyl salicylate | 220 |
| 2-n-pentylidene-3,3,5(3,5,5)-trimethylcyclopentanone | 100 |
| Phenyl ethyl alcohol | 90 |

COMPOSITION EXAMPLES

| | |
|---|---|
| Methyl ionone mixture (Isoraldein TM 70) | 75 |
| α-hexyl cinnamic aldehyde | 70 |
| Ylang oil | 60 |
| n-isoundecanol | 50 |
| Geranium oil Bourbon | 40 |
| Benzyl acetate | 40 |
| Indole, 10% in benzyl alcohol | 15 |
| Geranonitrile | 10 |

We claim:

1. A 2-alkylidene-3,3,5(3,5,5)-trimethyl cyclopentanone corresponding to the formula

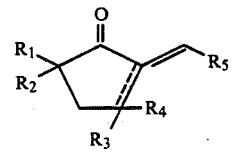

in which three of the substituents $R_1$ to $R_4$ are $CH_3$, one of the substituents $R_1$ to $R_4$ is H, $R_5$ is a saturated or unsaturated, linear or branched $C_1$–$C_7$ alkyl radical, and the double bond is in the endo or exo position to the cyclopentanone structure.

2. The cyclopentanone of claim 1 wherein $R_5$ contains from 2 to 5 carbon atoms.

3. The cyclopentanone of claim 1 wherein $R_5$ contains 3 carbon atoms.

4. The cyclopentanone of claim 1 which is 2-n-butylidene-3,3,5(3,5,5)-trimethyl cyclopentanone.

5. The cyclopentanone of claim 1 which is 2-n-butyl-3,5,5-trimethylcyclopent-2-ene-1-one.

6. The cyclopentanone of claim 1 which is 2-n-pentylidene-3,5,5(3,3,5)-trimethyl cyclopentanone.

7. In a perfume composition, the improvement wherein the composition contains from about 1 to about 50% by weight of a cyclopentanone of claim 1.

8. In a perfume composition, the improvement wherein the composition contains from about 1 to about 50% by weight of a cyclopentanone of claim 2.

9. In a perfume composition, the improvement wherein the composition contains from about 1 to about 50% by weight of a cyclopentanone of claim 3.

10. In a perfume composition, the improvement wherein the composition contains from about 1 to about 50% by weight of a cyclopentanone of claim 4.

11. The perfume composition of claim 7 wherein from about 2 to about 25% by weight of the cyclopentanone is present therein.

12. A method of improving the odor of a cosmetic, cleaning composition, disinfectant, or fabric treating composition comprising adding thereto an odor enhancing quantity of the cyclopentanone of claim 1.

* * * * *